US008808757B2

(12) United States Patent
Urschel et al.

(10) Patent No.: US 8,808,757 B2
(45) Date of Patent: Aug. 19, 2014

(54) HERBAL OINTMENT FOR MUSCULOSKELETAL AND JOINT-RELATED CONDITIONS

(75) Inventors: Michael J. Urschel, Adamstown, MD (US); Tara L. Urschel, Adamstown, MD (US); Kraig D. Moore, Upper Marlboro, MD (US)

(73) Assignee: Jaxsen's LLC, Adamstown, MD (US)

( * ) Notice: Subject to any disclaimer, the term of this patent is extended or adjusted under 35 U.S.C. 154(b) by 246 days.

(21) Appl. No.: 13/034,728

(22) Filed: Feb. 25, 2011

(65) Prior Publication Data

US 2011/0212193 A1 Sep. 1, 2011

Related U.S. Application Data

(60) Provisional application No. 61/308,424, filed on Feb. 26, 2010, provisional application No. 61/314,837, filed on Mar. 17, 2010.

(51) Int. Cl.
*A61K 36/00* (2006.01)
*A61K 36/82* (2006.01)
*A61K 36/8962* (2006.01)
*A61K 36/906* (2006.01)
*A61K 36/28* (2006.01)
*A61K 36/30* (2006.01)
*A61K 36/38* (2006.01)
*A61K 36/74* (2006.01)
*A61K 36/355* (2006.01)
*A61K 36/185* (2006.01)
*A61K 36/76* (2006.01)
*A61K 36/324* (2006.01)
*A61K 9/00* (2006.01)
*A61K 36/9066* (2006.01)
*A61K 36/484* (2006.01)
*A61K 9/06* (2006.01)
*A61K 36/71* (2006.01)

(52) U.S. Cl.
CPC .............. *A61K 36/30* (2013.01); *A61K 36/38* (2013.01); *A61K 36/74* (2013.01); *A61K 36/355* (2013.01); *A61K 36/28* (2013.01); *A61K 36/185* (2013.01); *A61K 36/76* (2013.01); *A61K 36/324* (2013.01); *A61K 9/0014* (2013.01); *A61K 36/9066* (2013.01); *A61K 36/484* (2013.01); *A61K 9/06* (2013.01); *A61K 36/71* (2013.01)
USPC ........... 424/725; 424/729; 424/756; 424/764; 424/778; 424/774

(58) Field of Classification Search
None
See application file for complete search history.

(56) References Cited

U.S. PATENT DOCUMENTS 6,333,056 B1 * 12/2001 Robinson ....................... 424/725
2004/0059110 A1 * 3/2004 Nakano et al. .................. 544/60
2009/0068255 A1 * 3/2009 Yu et al. ........................ 424/450

OTHER PUBLICATIONS

Riehemann, K., Behnke, B., Schulze-Osthoff, K., "Plant extracts from stinging nettle (*Urtica dioica*), an antirheumatic remedy, inhibit the proinflammatory transcription factor NF-KB," Federation of European Biochemical Societies (FEBS), 1999, pp. 89-94.
Ernst, E., "Christmas 2008: Seasonal Fayre, Frankincense: systematic review," British Medical Journal (BMJ) a2813, Nov. 23, 2008, pp. 1-4.
Thorne Research Inc., "*Boswellia serrata*," Alternative Medicine Review, vol. 13, No. 2, Jun. 2008, pp. 165-167.
Randall, C., Randall, H., Dobbs, F., Hutton, C., Sanders, H., "Randomized controlled trial nettle sting for treatment of base-of-thumb pain," Journal of the Royal Society of Medicine, vol. 93 Jun. 2000, pp. 305-309.
Buhrmann, C., Mobasheri, A., Busch, F., Aldinger, C. Stahlmann, R., Montaseri, A, Shakibaei, M., "Curcumin Modulates Nuclea Factor Kb (NF-KB)-mediated Inflammatio in Human Tenocytes in Vitro," The Journal of Biological Chemistry, vol. 286, No. 32, Aug. 12, 2011, pp. 28556-28566.
Wind, J., "Efficacy of feverfew as prophylactic treatment of migraine," Institute of Human Genetics, Free University, Amsterdam, British Medical Journal, vol. 291, Nov. 23, 1985, p. 1508.
George Wong, H.C., "Is feverfew a pharmacologic agent?," University of British Columbia, Letters Correspondence, Canadian Medical Association Journal (CMAJ), Jan. 12, 1999, vol. 160 No. 1, pp. 21-22.
Kim, D., Kim, SJ., Kang, SS., Jin, EJ., "Curcumin inhibits cellular condensation and alters microfilament organization during chondrogenic differentiation of limb bud mesenchymal cells," Experimental and Molecular Medicine, vol. 41, No. 9, Sep. 2009, pp. 656-664.

(Continued)

*Primary Examiner* — Chris R Tate
*Assistant Examiner* — Deborah Davis
(74) *Attorney, Agent, or Firm* — Duane Morris LLP

(57) ABSTRACT

An herbal ointment. The herbal ointment may include about 45 weight percent of herb-infused oil, water or alcohol, or any desired combination thereof, about 30 weight percent purified water, about 10 weight percent emulsifier wax, about 5 weight percent menthol, about 3 weight percent dimethyl isosorbide, about 2 weight percent glycerin, about 2 weight percent hydrogenated methyl abietate, about 0.5 weight percent *lonicera caprifolium* and *lonicera japanica* extract, about 0.5 weight percent tocopherol, about 0.35 weight percent vanillyl butyl ether, about 0.35 weight percent xanthan gum, about 0.3 weight percent citric acid 50% aqueous solution, and about 0.25 weight percent menthyl lactate, the herb-infused oil, water or alcohol including a 1:5 dilution of herbal extracts in a solvent, wherein the herbal extracts are of German Chamomile (*Matricaria recutita*), Valerian (*Valeriana officinalis*), Ginger (*Zingiber officinale* Roscoe), Peppermint (*Mentha×piperita*), Feverfew (*Tanacetum parthenium*), and Lemon Balm (*Melissa officinalis*).

14 Claims, No Drawings

(56) References Cited

OTHER PUBLICATIONS

Heptinstall, S., "Feverfew—an ancient remedy for modern times?," University Hospital, Nottingham, Journal of the Royal Society of Medicine, vol. 81, Jul. 1988, pp. 373-374.

Woolhouse, M., "Migraine and tension headache: A complementary and alternative medicine approach," Australian Family Physician, vol. 34, No. 8, Aug. 2005, pp. 647-650.

Toldy, A., Stadler, K., Sasvari, M, Jakus, J., Jung, ., Chung, H., Berkes, I., Nyakas, C., Radak, Z., "The effect of exercise and nettle supplementation on oxidative stress markers in the rat brain," Brain Research Bulletin 65, Feb. 21, 2005, pp. 487-493.

Modi, S., Lowder, D., "Medications for Migraine Prophylaxis," Brody School of Medicine, American Family Physician, vol. 73, No. 1, Jan. 1, 2006, pp. 72-78.

Johnson, E.S., Kadam, N.P., Hylands, D.M., Hylands, P.J., "Efficacy of feverfew as prophylactic treatment of migraine," British Medical Journal, vol. 291, Aug. 31, 1985, pp. 569-573.

Sterk, V., Buchele, B., Simmet, T., "Effect of food intake on the bioavailability of boswellic acids from a herbal preparation in healthy volunteers," Planta Medica, vol. 70, Aug. 19, 2004, pp. 1155-1160.

Shakibaei, M., Mobasheri, A., Buhrmann, C., "Curcumin synergizes with resveratrol to stimulate the MAPK signaling pathway in human articular chondrocytes in vitro," Genes & Nutrition—Springer, 201, vol. 6, ages 171-179.

Schulze-Tanzil, G., De Souza, P., Behnke, B., Klingelhoefer, S., Scheid, A. and M. Shakibaei, "Effects of the antirheumatic remedy Hox alpha—a new stinging nettle leaf extract—on matrix metalloproteinases in human chondrocytes in vitro," Histology and Histopathology Cellular and Molecular Biology, Jan. 28, 2002, vol. 17, pp. 477-485.

Thorne Research Inc., "Harpagophytum procumbens (Devil's Claw)," Alternative Medicine Review, vol. 13, No. 3, 2008, pp. 248-252.

Jang, MH., Lim, S., Han, SM., Park, HJ., Shin I., Kim, JW., Kim, NJ., Lee, JS., Kim, KA., Kim, CJ., "Harpagophytum procumbens suppresses lipopolysaccharide-stimulated expressions of cyclooxygenase-2 and inducible nitric oxide synthase in fibroblast cell line L929," Journal of Pharmacological Sciences, The Japanese Pharmacological Society, vol. 93, Sep. 1, 2003, pp. 367-371.

Csaki, C., Mobasheri, A., Shakibaei, M., "Synergistic chondroprotective effects of curcumin and resveratrol in human articular chondrocytes: inhibition of IL-1B-induced NF-KB-mediated inflammation and apoptosis," Arthritis Research & Therapy, 11:R165, Nov. 4, 2009, pp. 1-17.

Jaxsen's Natur' Way to Heal, Herbal Ingredients, http://www.jaxsens.com/herbal_ingredients.html, May 14, 2013.

* cited by examiner

HERBAL OINTMENT FOR MUSCULOSKELETAL AND JOINT-RELATED CONDITIONS

CROSS-REFERENCE TO RELATED APPLICATIONS

This application claims priority to U.S. Provisional Application 61/308,424, filed Feb. 26, 2010 and entitled APPARATUS AND METHODS FOR NON-INVASIVE PHYSICAL TREATMENT, and U.S. Provisional Application 61/314,837, filed Mar. 17, 2010 and entitled APPARATUS AND METHODS FOR NON-INVASIVE PHYSICAL TREATMENT AND OINTMENTS THEREFOR, the entire contents of which are hereby incorporated by reference.

BACKGROUND

Aging individuals generally begin to suffer from increased aches and pains arising out of the musculoskeletal system. Furthermore, injuries resulting from accidents, falls, sports and the like can impart damage to the musculoskeletal system that may manifest themselves not only as pain but also as stress, tension, general discomfort, and other maladies. Surgical procedures designed to remedy such symptoms and the causes thereof are generally expensive and invasive, causing further stress and discomfort to the patient, while not necessarily achieving the desired results. Therefore, an effective, non-invasive, and natural solution for relieving symptoms related to the musculoskeletal system is needed.

SUMMARY

According to at least one exemplary embodiment, an herbal ointment for musculoskeletal and joint-related conditions is provided. The ointment may include at least one of an herb-infused oil, water or alcohol having extracts from a plurality of herbs therein. The herbs may include, but are not limited to Comfrey (*Symphytum officinale*), Calendula Flower (*Calendula officinalis*), German Chamomile (*Matricaria recutita*), Stinging Nettle Leaf (*Urtica dioica*), *Arnica montana*, Devil's Claw (*Harpagophytum procumbens*), and Tumeric (*Curcuma longa*).

According to another exemplary embodiment, the herbs may include, but are not limited to, German Chamomile (*Matricaria recutita*), Valerian (*Valeriana officinalis*), Ginger (*Zingiber officinale* Roscoe), Peppermint (*Menthaxpiperita*), Feverfew (*Tanacetum parthenium*), and Lemon Balm (*Melissa officinalis*). Additional herbs included in the herbal ointment may include Licorice (*Glycyrrhiza glabra*), Boswellia (*Boswellia serrata*), White (*Salix alba*), Witch Hazel (*Hamamelis virginiana*), St. John's Wart (*Hypericum perforatum*), Black Cohosh (*Actaea racemosa*), Hops (*Humulus lupulus*), Saffron (*Crocus sativas*) and Passion Flower (*Passiflora incarnata*).

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

According to at least one exemplary embodiment, an herbal ointment is disclosed. The herbal ointment is adapted to be used for treatment and amelioration of symptoms related to musculoskeletal and joint-related conditions and injuries. Such conditions and injuries may include, but are not limited to: osteoarthritis; rheumatoid arthritis; gouty arthritis; muscle strains, sprains, and spasms; ligament sprains, strains or tears; as well as aches, pains and general discomfort related to the musculoskeletal system.

Additionally, the herbal ointment may be used by an individual to treat, for example, sports related injuries, degenerative joint diseases, and chronic muscle spasms as well as to speed the healing of injuries, maintain a desired level of health and to increase an individual's athletic performance. The herbal ointments may also be used for anti-inflammatory purposes.

A first exemplary embodiment of the herbal ointment may include a plurality of herbal extract ingredients directed towards treatment and amelioration of symptoms related to, for example, musculoskeletal and joint-related conditions and injuries. The herbs from which the ingredients may be extracted may include, but are not limited to, Comfrey (*Symphytum officinale*), Calendula Flower (*Calendula officinalis*), German chamomile (*Matricaria recutita*), Stinging Nettle Leaf (*Urtica dioica*), Wolf's bane (*Arnica montana*), Devil's Claw (*Harpagophytum procumbens*), and Turmeric (*Curcuma longa*).

The above-listed herbal active ingredients may be selected for their particular medicinal and therapeutic properties. Comfrey (*Symphytum officinale*) is an Allantoin containing anti-inflammatory herb that can speed healing of soft torn tissue, such as, but not limited to ligaments, tendons and muscles, and that can influence the course of bone ailments. Additionally, the allantoin contained in Comfrey (*Symphytum officinale*) may speed up the natural replacement of body cells. Calendula Flower (*Calendula officinalis*), has anti-inflammatory properties and can further control bleeding and soothe irritated tissue. German Chamomile (*Matricaria recutita*) is an inhibitor of the COX-2 enzyme, and has anti-inflammatory properties as well as spasmolytic, and anxiolytic effects, and can therefore induce muscle relaxation and relief of skeletal muscle spasms and associated pain. Stinging Nettle Leaf (*Urtica dioica*) can inhibit the breakdown of articular joint cartilage via the inhibition of matrix metalloproteinases as well as the inhibition of the NF-kappa B protein complex, and is therefore beneficial in arthritis treatment and rheumatism pain relief. Devil's Claw (*Harpagophytum procumbens*) has anti-inflammatory properties and can further preserve articular cartilage via down-regulation of Tumor Necrosis Factor Alpha and other interleukins. Devil's Claw (*Harpagophytum procumbens*) can thus reduce pain and aid in the treatment of arthritis as well as chronic low back pain. Tumeric (*Curcuma longa*) has anti-inflammatory, antiseptic and analgesic properties and can further have benefits for treatment of burns, cuts, and bruises as well as arthritic conditions. *Arnica montana* is an anti-inflammatory herb that can speed healing of soft torn tissue, such as ligaments, tendons and muscles. The above-listed herbal ingredients may be used to prepare an herbal-infused oil, water or alcohol, or any other desired combination thereof, prior to combination with any other desired active ingredients and any desired inactive ingredients.

A second exemplary embodiment of the herbal ointment may include a plurality of herbal extract ingredients directed towards relieving muscle pains and spasms. The herbs from which the ingredients may be extracted may include, but are not limited to, German chamomile (*Matricaria recutita*), Valerian (*Valeriana officinalis*), Ginger (*Zingiber officinale* Roscoe), Peppermint (*Mentha×piperita*), Feverfew (*Tanacetum parthenium*), and Lemon balm (*Melissa officinalis*).

The above-listed herbal active ingredients may be selected for their particular medicinal and therapeutic properties. German Chamomile (*Matricaria recutita*) is an inhibitor of the COX-2 enzyme, and has anti-inflammatory properties as well as spasmolytic, and anxiolytic effects, and can therefore induce muscle relaxation and relief of skeletal muscle spasms. Valerian (*Valeriana officinalis*) has anti-spasmodic properties, and is also a sedative and anticonvulsant. Ginger (*Zingiber officinale* Roscoe) has analgesic effects and can also be used to reduce inflammation and reduce pains from arthritis. Peppermint (*Mentha×piperita*) has soothing and anti-inflammatory properties on the skin surface and is capable of easily penetrating the skin and tissues to provide anti-spasmodic and relaxant effects on the muscles. Feverfew (*Tanacetum parthenium*) likewise has analgesic and anti-spasmodic properties and is beneficial for treatment of arthritis. Lemon balm (*Melissa officinalis*) has analgesic properties as well as anxiolytic and relaxant effects.

Additional active ingredients may be included in the embodiments of the herbal ointment. Such ingredients may include, but are not limited to: menthol, dimethyl isosorbide, hydrogenated methyl abietate, vanillyl butyl ether, and menthyl lactate. These ingredients have been selected to further enhance the efficacy of the herbal ointment. Menthol is a topical analgesic having local anesthetic and counter-irritant qualities. Vanillyl butyl ether is a warming agent, while menthyl lactate is a cooling agent, and the combination of the two ingredients can be used to provide simultaneous heating sensations and cooling sensations to the area where the herbal ointment is applied. Dimethyl isosorbide is a penetrating agent that can facilitate penetration of the skin by the herbal ointment, thereby enhancing the delivery of the active ingredients of the herbal ointment to the desired areas. Hydrogenated methyl abietate is a delayed release agent and film former, and functions as a fixative, carrier and stabilizer for the herbal ointment.

In addition to the ingredients described above, embodiments of the herbal ointment may also include, if desired, at least one of the following ingredients: camphor, beeswax, titanium dioxide, pokeroot (*phytolacca*), cleavers (*galium aparine*), licorice (*glycyrrhiza glabra*), autumn saffron crocus (*crocus sativus*), boswellia, bromelain enzymes, white willow (*salix alba*), witch-hazel (*Hamamelis virginiana*), capsaicin, St. John's Wort (*hypericum perforatum*), black cohosh (*actaea racemosa*), hops (*humulus lupulus*), passionflower (*passiflora*), carotenoids, and bioflavonoids.

The preparation of the herbal ointment may involve a plurality of steps. The herbs of the above-described embodiments, as well as any other desired herbs, may be used to prepare an herb-infused oil, an herb-infused water or an herb-infused alcohol, or any desired combination thereof, such as, but not limited to an herb-infused oil and water combination. The herb-infused oil, water or alcohol, or combination thereof, may further be combined with the additional active ingredients, as well as any other desired active or inactive ingredients, so as to form the herbal ointment.

To prepare the herb-infused oil, water or alcohol, or any desired combination thereof, the herbs of the above-described embodiments may be placed into a solvent in a ratio of approximately 1 part herbs to 5 parts solvent so as to form a 1:5 dilution. The solvent may be, but is not limited to, fractionated coconut oil, distilled water, an alcohol, or glycerol. Regarding the infused oil preparation, the resultant mixture may be heated to a temperature of between about 100 degrees Fahrenheit (about 37.78° C.) to about 115 degrees Fahrenheit (about 46.11° C.). The mixture may be maintained at this temperature for approximately two weeks and may be stirred for approximately 15 minutes every hour during this time. The extraction of the herbal ingredients from their respective herbs and into the solvent may thus be optimized. Next, the resultant infusion may be pressed through a press, for example a tincture press, so as to obtain a pressed infusion. The pressed infused oil, water or alcohol, or combination thereof, may then be stored in a dark, cool and dry place for approximately 24-48 hours. Subsequently, the pressed infused oil, water or alcohol, or combination thereof, may be strained through a porous medium, for example a cheese cloth, gauze, mesh sieve or the like. The resultant herb-infused oil, water or alcohol, or combination thereof, may then be stored in a dark, cool and dry place, or combined with the additional active ingredients as well as any other desired active or inactive ingredients, so as to form the herbal ointment. Alternatively, the herb extraction may be prepared by Spagyric methods, or any other desired solvent extraction processes.

To prepare the herbal ointment, the combination of herbal infused oil, water or alcohol, or combinations thereof, with the additional active ingredients as well as any other desired active or inactive ingredients, may be performed by formation of three separate phases, wherein certain desired ingredients are combined so as to form a first phase, other certain desired ingredients are combined separately from the first phase so as to form a second phase, and yet other certain desired ingredients are combined separately from the first and second phases so as to form a third phase. Upon formation of the three separate phases, the phases may be treated and combined according to the below-described procedure.

Desired ingredients for the first phase and their corresponding approximate proportions by weight relative to the resultant weight of the herbal ointment, may be as follows:

| Ingredient | % w/w (approx.) |
| --- | --- |
| Purified water | 30.75 |
| Citric acid 50% aqueous solution | 0.3 |
| Honeysuckle extract (*Lonicera caprifolium* and *Lonicera japanica*) | 0.5 |
| Xanthan gum | 0.35 |
| Menthol | 5.0 |
| Glycerin 99.7% | 2.0 |

Desired ingredients for the second phase and their corresponding approximate proportions by weight relative to the resultant weight of the herbal ointment, may be as follows:

| Ingredient | % w/w (approx.) |
| --- | --- |
| Herb-infused oil/water/alcohol | 45.0 |
| Dimethyl isosorbide | 3.0 |

-continued

| Ingredient | % w/w (approx.) |
|---|---|
| Tocopherol (Vitamin E) | 0.5 |
| Hydrogenated methyl abietate | 2.0 |
| Emusifier wax | 10.0 |

Desired ingredients for the third phase and their corresponding approximate proportions by weight relative to the resultant weight of the herbal ointment, may be as follows:

| Ingredient | % w/w (approx.) |
|---|---|
| Vanillyl butyl ether | 0.35 |
| Menthyl lactate | 0.25 |

The ingredients for the first phase may be combined in a first vessel. The proportion of citric acid may be adjusted such that the pH of the solution is approximately 5.5±0.5. The solution may then be heated to approximately 80° C. until the solution is uniform. The ingredients of the second phase may be combined in a second vessel and heated to approximately 75° C.-78° C. until the solution is substantially uniform. The solution of the second phase may then be added to the solution of the first phase and stirred for approximately 5 minutes, for example by a propeller or vane disposed in the vessel, as well as by side sweep mixing. Subsequently, the combined first and second phase solution may be stirred continuously for about 5-10 minutes, for example by a homogenizer at about 5,000 rpm, or at any other desired speed. The mixing may also be facilitated by a propeller or vane disposed in the vessel, as well as by side sweep mixing. Subsequently, the solution may be cooled to approximately 40° C.-45° C., at which point the ingredients of the third phase may be added, with continuous stirring of the solution. The resultant herbal ointment may then be cooled to approximately 30° C. and stirring may continue until the herbal ointment is substantially uniform.

The above described-embodiments of the herbal ointment may be applied directly to the skin of a subject, proximate to the affected area, so as to provide relief for the symptoms related to the conditions described herein. However, other modes of application may also be used as desired. For example, the embodiments of the herbal ointment may be used in conjunction with an applicator, such as a roll-on stick, spray or any other desired applicator. The embodiments of the herbal ointment may also be used in conjunction with a patch, such as a transdermal patch. The transdermal patch (single layer drug-in-adhesive or multi-layer drug-in-adhesive systems) may include a reservoir layer that contains the herbal ointment, an adhesive portion for adhering to the skin of the subject around the affected area, a backing portion for handling the transdermal patch, and an occlusive layer that may facilitate increasing the humidity around the application site, thereby facilitating the increase of transdermal absorption of the herbal ointment. The embodiments of the herbal ointment may also be impregnated into an electrode pad, which may be any type of electrode pad known in the art and may be a type of electrode pad that does not require a conductive gel for operation.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An herbal ointment for relief of symptoms related to muscular, musculoskeletal or joint-related conditions, comprising:
   herbal extracts infused in a solvent from a plurality of herbs that include Comfrey, Stinging Nettle Leaf, Devil's Claw, German Chamomile, *Calendula* Flower, Turmeric, and *Arnica montana*, said herbal extracts being effective to provide relief of said symptoms;
   a penetrating agent to facilitate penetration of skin by the herbal ointment, thereby enhancing the delivery of the active ingredients of the herbal ointment; and
   a delayed release agent to provide delayed release of at least a portion of the herbal ointment to provide prolonged relief of said symptoms.

2. The herbal ointment of claim 1, wherein said plurality of herbs further includes *Boswellia*.

3. The herbal ointment of claim 1, wherein the penetrating agent is dimethyl isosorbide.

4. The herbal ointment of claim 3, wherein the dimethyl isosorbide comprises about 3 weight percent of the herbal ointment.

5. The herbal ointment of claim 1, wherein the delayed release agent is hydrogenated methyl abietate.

6. The herbal ointment of claim 5, wherein the hydrogenated methyl abietate comprises about 2 weight percent of the herbal ointment.

7. The herbal ointment of claim 1, further comprising a topical analgesic.

8. The herbal ointment of claim 7, wherein the topical analgesic is selected from the group consisting of menthol and extractions of the herb peppermint.

9. The herbal ointment of claim 7, wherein the topical analgesic is menthol in an amount that is about 5 weight percent of the herbal ointment.

10. The herbal ointment of claim 1, further comprising a cooling agent to provide a cooling sensation and a warming agent to provide a warming sensation.

11. The herbal ointment of claim 10, wherein the cooling agent is menthyl lactate and comprises about 0.25 weight percent of the herbal ointment.

12. The herbal ointment of claim 10, wherein the warming agent is vanillyl butyl ether and comprises about 0.35 weight percent of the herbal ointment.

13. The herbal ointment of claim 1, wherein the herbal extracts infused in the solvent are extracted using a spagyric method of extraction.

14. An herbal ointment for relief of symptoms related to muscular, musculoskeletal or joint-related conditions, comprising:
   herbal extracts infused in a solvent by a spagyric extraction method from a plurality of herbs that include Comfrey, Stinging Nettle Leaf, Devil's Claw, German Chamomile, *Calendula* Flower, Turmeric, and *Arnica montana*, said herbal extracts infused in a solvent being effective to provide relief of said symptoms;
   about 3 weight percent dimethyl isosorbide to facilitate penetration of skin by the herbal ointment, thereby enhancing the delivery of the active ingredients of the herbal ointment;

about 2 weight percent hydrogenated methyl abietate to provide delayed release of at least a portion of the herbal ointment to provide prolonged relief of said symptoms;

about 5 weight percent menthol;

about 0.25 weight percent menthyl lactate to provide a cooling sensation; and about 0.35 weight percent vanillyl butyl ether to provide a warming sensation.

\* \* \* \* \*